United States Patent

Weuthen

Patent Number: 5,955,587
Date of Patent: Sep. 21, 1999

[54] PROCESS FOR PREPARING ALKYL OLIGOGLUCOSIDES WITH A HIGH DEGREE OF OLIGOMERIZATION

[75] Inventor: Manfred Weuthen, Solingen, Germany

[73] Assignee: Henkel Kommanditgesellschaft auf Aktien, Duesseldorf, Germany

[21] Appl. No.: 08/952,643

[22] PCT Filed: Feb. 23, 1996

[86] PCT No.: PCT/EP96/00752

§ 371 Date: Nov. 20, 1997

§ 102(e) Date: Nov. 20, 1997

[87] PCT Pub. No.: WO96/37501

PCT Pub. Date: Nov. 28, 1996

[30] Foreign Application Priority Data

May 26, 1995 [DE] Germany .......................... 195 19 384

[51] Int. Cl.⁶ .............................. C07G 3/00; C07H 1/00
[52] U.S. Cl. .................... 536/18.6; 536/18.5; 536/124
[58] Field of Search ................... 536/18.5, 18.6, 536/124

[56] References Cited

U.S. PATENT DOCUMENTS

| | | | |
|---|---|---|---|
| 4,866,165 | 9/1989 | Lüders | 536/18.6 |
| 5,612,467 | 3/1997 | Weuthen et al. | 536/18.6 |
| 5,698,684 | 12/1997 | Hill et al. | 536/18.6 |

FOREIGN PATENT DOCUMENTS

| | | |
|---|---|---|
| WO93/10133 | 5/1993 | WIPO. |
| WO94/25475 | 11/1994 | WIPO. |
| WO95/01360 | 1/1995 | WIPO. |

OTHER PUBLICATIONS

H. Hensen, Skin Care Forum, p. 1 (Oct. 1992).

Balzer, et al., Seifen–Öle–Fette–Wachse, 118: pp. 894, 896, 898, 900, 903, 904 (1992).

B. Brancq, Seifen–Öle–Fette–Wachse, 118: pp. 905–906 (1992).

*Primary Examiner*—Gary L. Kunz
*Attorney, Agent, or Firm*—Ernest G. Szoke; Wayne C. Jaeschke; Steven J. Trzaska

[57] ABSTRACT

A process for producing alkyl oligoglucosides having a high degree of polymerization involving: (a) providing a fatty alcohol; (b) providing a glucose component; (c) mixing the fatty alcohol and glucose component; (d) acetylizing the reaction mixture by adding an acid catalyst to the mixture; (e) continuously distilling off water from the reaction mixture during acetylization; (f) neutralizing the acid catalyst upon completion of acetylization; (g) removing unreacted fatty alcohol from the reaction mixture; (h) post-polymerizing the reaction mixture to form a final alkyl oligoglucoside product; and (i) neutralizing any remaining acid catalyst and removing any unreacted fatty alcohol from the reaction mixture.

10 Claims, No Drawings

PROCESS FOR PREPARING ALKYL OLIGOGLUCOSIDES WITH A HIGH DEGREE OF OLIGOMERIZATION

This application is a 371 of PCT/EP96/00752 filed Feb. 23, 1996.

BACKGROUND OF THE INVENTION

1. Field of the Invention

This invention relates to a process for the production of alkyl oligoglucosides with a high DP degree (1.6 to 2.0), in which alkyl polyglucosides with a low DP degree (<1.6) are subjected to post-polymerization, and to the use of the alkyl oligoglucosides thus produced as defoamers in machine bottle washing.

2. Discussion of Related Art

Alkyl oligoglycosides, more particularly alkyl oligoglucosides, are nonionic surfactants which are acquiring increasing significance by virtue of their excellent detergent properties and their high ecotoxicological compatibility. The production and use of these compounds have been described just recently in a number of synoptic articles, of which the articles by H. Hensen in Skin Care Forum, 1 (October 1992), D. Balzer and N. Ripke in Seifen-Öle-Fette-Wachse 118, 894 (1992) and B. Brancq in Seifen-Öle-Fette-Wachse 118, 905 (1992) are cited as representative.

Alkyl oligoglucosides are produced from fatty alcohols and glucose or glucose sirup which are acetalized in the presence of acidic catalysts. To displace the reaction equilibrium onto the product side, the less expensive component, the fatty alcohol, is normally introduced in excess and the water of reaction is continuously distilled off. Thereafter, the acidic catalyst is neutralized to avoid secondary reactions and the excess fatty alcohol is distilled off in vacuo.

Now, 1 mole of fatty alcohol and 1 mole of glucose come together non-selectively during the reaction. The glucose also undergoes likewise acid-catalyzed self-condensation in competition with the formation of these monoglucosides, resulting in the formation of polysugars. In addition, the glucose reacts with the alkyl glucosides already formed to form oligoglucosides. This results in the formation of a complex mixture of mono-, di-, tri-, tetra- and oligoglucosides which, in addition, contains considerable amounts of polyglucose. Apart from the alkyl chain length, the applicational properties of the glucosides, for example their solubility, cold cloud point, foam stability and thickenability, are also determined by the homolog distribution which is defined by a ratio known as the degree of polymerization (DP).

Commercial alkyl oligoglucosides generally have a low DP of 1.2 to 1.6. This is attributable above all to technical reasons because higher degrees of oligomerization can normally only be established when the fatty alcohol excess in the acetalization is small. However, this is only possible to a limited extent on account of the high initial viscosity of the mixtures.

Another problem is that a small excess of fatty alcohol promotes the formation of unwanted polyglucose and significantly impairs the color quality of both the bleached and the unbleached products. At the same time, however, there is a need in the market place for alkyl oligoglucosides with a high DP which can be superior in some respects to the commercial products available with their low degrees of oligomerization.

Accordingly, the complex problem addressed by the present invention was to provide a process for the production of alkyl oligoglucosides with a high degree of oligomerization by which the problems presented by the initial viscosity of the reaction mixtures, the high polysugar content and the inadequate color quality could be solved at one and the same time. In addition, in view of the occasionally inadequate alkali stability of the products, the alkyl oligoglucosides produced by the process according to the invention would have improved defoaming properties in machine bottle washing, even under strongly basic conditions.

DESCRIPTION OF THE INVENTION

The present invention relates to a process for the production of alkyl oligoglucosides with a high degree of oligomerization, in which (a) fatty alcohols corresponding to formula (I):

$$R^1OH \qquad (I)$$

in which $R^1$ is an alkyl radical containing 6 to 22 carbon atoms, and glucose in a molar ratio of 3:1 to 10:1 are subjected to acid-catalyzed acetalization at temperatures of 90 to 120° C., (b) the water of reaction is continuously distilled off, (c) on completion of the reaction, 0 to 90 mole-% of the acidic catalyst is neutralized, (d) the unreacted fatty alcohol is removed in such a quantity that the molar ratio of the fatty alcohol still remaining to the glucose, based on the starting quantity is still 1:1 to 3:1, (e) the reaction mixture is subjected to post-polymerization at temperatures of 90 to 120° C., (f) the remaining quantity of acidic catalyst is neutralized and the remaining quantity of unreacted fatty alcohol is removed.

It has surprisingly been found that the process according to the invention gives alkyl oligoglucosides which have a high degree of oligomerization of 1.6 to 2.0 without the products being adversely affected by a high polyglucose content or unsatisfactory color quality. At the same time, the otherwise unavoidable problem of a high initial viscosity is solved by the proposed process so that high volume-time yields and economic operation are possible. The invention includes the observation that the alkyl oligoglucosides obtainable by the process according to the invention have improved alkali stability in relation to comparable homologs with a lower DP.

Fatty Alcohols

Typical examples of fatty alcohols, which may be used as starting materials in accordance with the present invention, are caproic alcohol, caprylic alcohol, 2-ethylhexyl alcohol, capric alcohol, lauryl alcohol, isotridecyl alcohol, myristyl alcohol, cetyl alcohol, stearyl alcohol, isostearyl alcohol and behenyl alcohol and the technical mixtures thereof obtained, for example, in the high-pressure hydrogenation of technical methyl esters based on fats and oils or aldehydes from Roelen's oxo synthesis and as monomer fraction in the dimerization of unsaturated fatty alcohols. Technical fatty alcohols containing 8 to 10 or 12 to 18 carbon atoms, such as, for example, hydrogenated head-fractionated fatty alcohol, coconut oil fatty alcohol, palm oil fatty alcohol, palm kernel oil fatty alcohol or tallow fatty alcohol are preferred.

Acidic Catalysts

Suitable acidic catalysts are, for example, sulfuric acid, alkyl sulfuric acid semiesters, alkyl benzene sulfonic acids, such as for example p-toluene sulfonic acid or dodecyl benzene sulfonic acid, and sulfosuccinic acid. The acidic catalysts are normally used in a quantity of 0.1 to 5% by weight and preferably in a quantity of 0.5 to 2% by weight, based on the starting materials.

Acetalization

The acetalization may be carried out by methods known per se. Normally, the fatty alcohol is initially introduced together with the acidic catalyst, a suspension of glucose in fatty alcohol is added and the whole is heated to the reaction temperature. However, it is also possible initially to prepare a homogeneous suspension of fatty alcohol and glucose, to heat the reaction mixture and, at the same time, to add a solution of the acidic catalyst in fatty alcohol. This phase is not critical so that other procedures may also be adopted. Particular reference is made in this connection to the use of aqueous glucose sirup, which is freed from water before acetalization in the presence or absence of the fatty alcohol, and to the use of spray-dried dextrose sirup or dextrose sirup dried with superheated steam. Instead of the direct reaction of glucose and fatty alcohol, it is also possible to choose the route known as "transacetalization" which proceeds via the formation of butyl glucosides as intermediate products. The reaction is carried out below the caramelization temperature of the sugar at around 100 to 120° C. and preferably under a reduced pressure of 0.1 to 100 mbar. For kinetic reasons, continuous removal of the water formed during the condensation from the reaction mixture is highly advisable.

After the acetalization, preferably when the residual glucose content has fallen below 3% by weight and, more particularly, 1% by weight, the acidic catalyst is neutralized in known processes. According to the present invention, this step is either omitted or only partly carried out, i.e. for example to a level of about 10 to 90 mole-%. The neutralization bases used are, primarily, alkali metal hydroxides and/or alkaline earth metal oxides, preferably aqueous sodium hydroxide solution and magnesium oxide.

Post-Polymerization

Up to this stage of the process, therefore, the advantages of a large excess of fatty alcohol have been utilized. The problem of the high paste viscosity, the formation of undesirably large amounts of polyglucose and the lack of bleachability could thus be avoided. Now, however, the crude alkyl oligoglucosides present as intermediate products do not yet have the high DP required.

However, the partial neutralization or non-neutralization of the catalyst has ensured that, following removal of part of the fatty alcohol, sufficient $H^+$ ions are available to support the post-polymerization. If the ratio by weight of fatty alcohol to glucose at the beginning of the reaction was still 3:1 to 10:1 and preferably 6:1 to 8:1, fatty alcohol is now distilled off in vacuo in such a quantity that, based on the starting quantity, a ratio of 1:1 to 3:1 and preferably 1.5:1 to 2.5:1 is obtained. The post-polymerization of the reaction mixture to form alkyl oligoglucosides with—in comparative terms—a relatively high degree of oligomerization may be carried out in a separate step under the reaction conditions mentioned above. In practice, however, this is generally not necessary because the post-polymerization even takes place under the conditions of partial removal of the fatty alcohol and provides the required results. In overall terms, the post-polymerization is continued until a DP of 1.6 to 2.0 and preferably 1.7 to 1.9 is established. The complete neutralization of the catalyst, the removal of the excess alcohol remaining and the alkaline bleaching step may then be carried out in known manner.

COMMERCIAL APPLICATIONS

The alkyl oligoglucosides obtainable by the process according to the invention are light-colored and have a degree of oligomerization of 1.6 to 2.0. They are suitable for the production of laundry detergents, dishwashing detergents and cleaning products and hair-care and body-care products in which they may be present in quantities of 1 to 50% by weight and preferably 5 to 35% by weight, based on the particular product. By virtue of their particular alkali stability, the alkyl oligoglucosides are particularly suitable as defoamers for the machine washing of milk and beer bottles.

The following examples are intended to illustrate the invention without limiting it in any way.

PRODUCTION EXAMPLES

Comparison Example C1

A mixture of 1964 g (10.5 moles) of dodecanol and 630 g (3.5 moles) of glucose was introduced into a 3 liter stirred reactor and heated to a temperature of 110° C. under a reduced pressure of 20 mbar. 6.6 g (20 mmoles) of dodecyl benzene sulfonic acid were then added dropwise over a period of 10 minutes. After a reaction time of 9 h, the reaction was terminated by addition of 1 ml (19 mmoles) of 50% by weight aqueous sodium hydroxide solution and 3.2 g (80 mmoles) of magnesium oxide. The mixture was transferred to a thin-layer evaporator and freed from the excess fatty alcohol under a reduced pressure of 0.1 mbar and at a bottom temperature of 165° C. 915 g of product were obtained. The product was dissolved in 900 g of water at 90° C. and, after the addition of 27 ml of 50% by weight aqueous sodium hydroxide solution, was bleached over a period of 24 h by addition of 38 ml of 35% by weight hydrogen peroxide. The characteristic data of the product are shown in Table 1 (percentages as % by weight).

Example 1

As in Comparison Example C1, 2235 g (12 moles) of dodecanol and 360 g (2.0 moles) of glucose were heated to a temperature of 110° C. under a reduced pressure of 20 mbar. 4 g (12 mmoles) of dodecyl benzene sulfonic acid were then added dropwise over a period of 10 minutes. After a reaction time of 6 h, 0.6 mole (7.2 mmoles) of 50% by weight aqueous sodium hydroxide solution were added to the mixture and the pressure was reduced to 0.05 mbar. 1560 g (8.4 moles) of dodecanol were then distilled off, initially at a bottom temperature of 95° C. On completion of the distillation, the pressure was increased to 2 mbar and the reaction mixture was stirred for another hour at 105° C. The reaction was terminated by addition of 0.34 g (4.1 mmoles) of 50% by weight sodium hydroxide solution and 1.9 g (48 mmoles) of magnesium oxide. The remaining fatty alcohol was removed under a vacuum of 0.1 mbar and at a bottom temperature of 165° C. 608 g of product were obtained and were bleached as in C1. The characteristic data are set out in Table 1.

Example 2

As in Comparison Example C1, 2235 g (12 moles) of dodecanol and 360 g (2.0 moles) of glucose were heated to a temperature of 110° C. under a reduced pressure of 20 mbar. 4 g (12 mmoles) of dodecyl benzene sulfonic acid were then added dropwise over a period of 10 minutes. After a reaction time of 6 h, 0.6 mole (7.2 mmoles) of 50% by weight aqueous sodium hydroxide solution were added to the mixture and the pressure was reduced to 0.05 mbar. 1730 g (9.3 moles) of dodecanol were then distilled off, initially at a bottom temperature of 95° C. On completion of the distillation, the pressure was increased to 2 mbar and the reaction mixture was stirred for another hour at 105° C. The reaction was terminated by addition of 0.34 g (4.1 mmoles) of 50% by weight sodium hydroxide solution and 1.9 g (48 mmoles) of magnesium oxide. The remaining fatty alcohol was removed under a vacuum of 0.1 mbar and at a bottom temperature of 165° C. 596 g of product were obtained and were bleached as in C1. The characteristic data are set out in Table 1.

TABLE 1

Test results (percentages as % by weight)

| Characteristic data | Comparison Example C1 | Example 1 | Example 2 |
| --- | --- | --- | --- |
| Monoglucosides [%] | 51.9 | 42.0 | 37.3 |
| Diglucosides [%] | 16.7 | 21.5 | 20.1 |
| Triglucosides [%] | 8.9 | 12.7 | 12.8 |
| Tetraglucosides [%] | 7.2 | 8.6 | 9.5 |
| Pentaglucosides [%] | 3.7 | 5.5 | 8.5 |
| Hexaglucosides [%] | 1.8 | 1.8 | 4.7 |
| Residual alcohol [%] | <0.2 | <0.2 | <0.2 |
| Polyglucose [%] | 6.9 | 2.6 | 3.3 |
| DP | 1.65 | 1.71 | 1.92 |
| Gardner color value | 5.0 | 2.0 | 2.0 |

APPLICATION EXAMPLES

Method.

In a double-walled 2-liter measuring cylinder, 300 ml of a 1% by weight sodium hydroxide solution were heated to 65° C. The particular foam-suppressing additive selected A=cocoalkyl oligoglucoside, DP=1.92, of Example 2 (invention)

B=cocoalkyl oligoglucoside, DP=1.3 (comparison)

were then added in the quantities shown below. Using a laboratory flow inducer, the liquid was circulated at a rate of 4 l/min. By means of a glass tube connected to a pump, the test solution was taken in about 5 mm above the bottom of the measuring cylinder and was returned in free fall through a second tube arranged at the 2000 ml mark. After 30 s, 1 ml of a 1% by weight aqueous solution of tetrapropylene benzenesulfonate triethanolammonium salt (hereinafter referred to as "test foamer") was first introduced into the liquor and the volume formed by liquid and foam was determined after another 30 s. More test foamer was added at 1 minute intervals and the foam/liquid volume formed after 30 s was determined. This step-by-step cycle of adding the test foamer and measuring the foam volume was continued until the surfactant solution had foamed to 2000 ml in the measuring cylinder. The results are set out in Table 2.

TABLE 2

| Foam [ml] | Defoamer effect Quantity of test foamer [ml] | | | | | | | | |
| --- | --- | --- | --- | --- | --- | --- | --- | --- | --- |
| | 0 | 1 | 5 | 10 | 12 | 14 | 16 | 18 | 20 |
| A | 300 | 300 | 380 | 480 | 540 | 600 | 720 | 1000 | 1680 |
| B | 300 | 300 | 380 | 490 | 560 | 640 | 890 | 1300 | 2000 |

It can be seen that the alkyl oligoglucosides with a relatively high DP have a significantly better defoamer effect.

I claim:

1. A process for producing alkyl oligoglucosides having a high degree of polymerization comprising:

(a) providing a fatty alcohol corresponding to formula I:

$$R^1OH \qquad (I)$$

wherein $R^1$ is an alkyl radical having from 6 to 22 carbon atoms;

(b) providing a glucose component;

(c) mixing the fatty alcohol and glucose component in an initial molar ratio of from 3:1 to 10:1 to form a reaction mixture;

(d) acetylizing the reaction mixture at a temperature of from 90 to 120° C. by adding an acid catalyst to the mixture;

(e) continuously distilling off water from the reaction mixture during acetylization;

(f) neutralizing up to 90 mole-% of the acid catalyst upon completion of acetylization;

(g) removing unreacted fatty alcohol from the reaction mixture until a final molar ratio of fatty alcohol to glucose component of from 1:1 to 3:1 is achieved;

(h) post-polymerizing the reaction mixture at a temperature of from 90 to 120° C. to form a final alkyl oligoglucoside product; and (i) neutralizing any remaining acid catalyst and removing any unreacted fatty alcohol from the reaction mixture.

2. The process of claim 1 wherein the initial molar ratio of fatty alcohol to glucose component is from 6:1 to 8:1.

3. The process of claim 1 wherein the final molar ratio of fatty alcohol to glucose component is from 1.5:1 to 2.5:1.

4. The process of claim 1 wherein the final alkyl oligoglucoside product has a degree of polymerization of from 1.6 to 2.0.

5. The process of claim 1 wherein the final alkyl oligoglucoside product has a degree of polymerization of from 1.7 to 1.9.

6. The process of claim 1 wherein $R^1$ contains from 8 to 10 carbon atoms.

7. The process of claim 1 wherein $R^1$ contains from 12 to 18 carbon atoms.

8. The process of claim 1 wherein the acid catalyst is employed in an amount of from 0.1 to 5% by weight.

9. The process of claim 1 wherein the acid catalyst is employed in an amount of from 0.5 to 2% by weight.

10. The process of claim 1 wherein the acetylization is carried out at a temperature of from 100 to 120° C. and a pressure of from 0.1 to 100 mbar.

* * * * *